(12) United States Patent
Buckley et al.

(10) Patent No.: US 11,672,682 B2
(45) Date of Patent: Jun. 13, 2023

(54) ENDOPROSTHESIS HAVING ALIGNED LEGS FOR EASE OF CANNULATION

(71) Applicant: W. L. Gore & Associates, Inc., Newark, DE (US)

(72) Inventors: Kyle R. Buckley, Flagstaff, AZ (US); Benjamin I. Espen, Flagstaff, AZ (US); Douglas C. Helsel, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 400 days.

(21) Appl. No.: 16/900,387

(22) Filed: Jun. 12, 2020

(65) Prior Publication Data
US 2020/0306068 A1 Oct. 1, 2020

Related U.S. Application Data

(60) Continuation of application No. 16/266,308, filed on Feb. 4, 2019, now Pat. No. 10,695,203, which is a
(Continued)

(51) Int. Cl.
*A61F 2/95* (2013.01)
*A61F 2/954* (2013.01)
(Continued)

(52) U.S. Cl.
CPC ............... *A61F 2/954* (2013.01); *A61F 2/07* (2013.01); *A61F 2/97* (2013.01);
(Continued)

(58) Field of Classification Search
CPC .. A61F 2/07; A61F 2/954; A61F 2/958; A61F 2002/065; A61F 2002/072;
(Continued)

(56) References Cited

U.S. PATENT DOCUMENTS 4,878,906 A * 11/1989 Lindemann ............. A61F 2/958
623/3.18
5,405,378 A * 4/1995 Strecker .................... A61F 2/90
623/1.42
(Continued)

FOREIGN PATENT DOCUMENTS

CN       1354641 A      6/2002
CN     104093378 A      10/2014
(Continued)

OTHER PUBLICATIONS

Joh, Jin Hyun, Hyung-Joon Ahn, and Ho-Chul Park. "Reference diameters of the abdominal aorta and iliac arteries in the Korean population." Yonsei medical journal 54.1 (2013): 48. (Year: 2013).
(Continued)

*Primary Examiner* — Ryan J. Severson

(57) ABSTRACT

The present disclosure is directed to a branched endoprosthesis comprising a graft component and at least one support component. In various embodiments, the branched endoprosthesis comprises a body portion and a plurality of leg portions, wherein the legs are in an aligned configuration for ease of cannulation. In various embodiments, at least one leg is in an open configuration for ease of cannulation. Cannulation methods are also described.

14 Claims, 6 Drawing Sheets

Related U.S. Application Data continuation of application No. 15/632,741, filed on Jun. 26, 2017, now Pat. No. 10,195,063, which is a division of application No. 13/740,457, filed on Jan. 14, 2013, now Pat. No. 9,687,371.

(60) Provisional application No. 61/598,773, filed on Feb. 14, 2012.

(51) Int. Cl.
*A61F 2/07* (2013.01)
*A61F 2/97* (2013.01)
*A61F 2/06* (2013.01)

(52) U.S. Cl.
CPC ... *A61F 2002/065* (2013.01); *A61F 2002/072* (2013.01); *A61F 2002/9511* (2013.01); *A61F 2210/009* (2013.01); *A61F 2210/0014* (2013.01); *A61F 2220/005* (2013.01); *A61F 2220/0058* (2013.01)

(58) Field of Classification Search
CPC ...... A61F 2002/9511; A61F 2210/0014; A61F 2210/009; A61F 2220/005; A61F 2220/0058
See application file for complete search history.

(56) References Cited

U.S. PATENT DOCUMENTS

| | | | |
|---|---|---|---|
| 5,755,769 A * | 5/1998 | Richard | A61F 2/90 623/1.2 |
| 6,102,940 A | 8/2000 | Robichon et al. | |
| 6,165,210 A | 12/2000 | Lau et al. | |
| 6,203,550 B1 | 3/2001 | Olson | |
| 6,254,628 B1 * | 7/2001 | Wallace | A61B 17/1214 606/108 |
| 6,264,662 B1 | 7/2001 | Lauterjung | |
| 6,352,561 B1 * | 3/2002 | Leopold | A61F 2/07 623/1.11 |
| 6,368,345 B1 | 4/2002 | Dehdashtian et al. | |
| 6,551,350 B1 * | 4/2003 | Thornton | A61F 2/07 606/198 |
| 6,733,521 B2 | 5/2004 | Chobotov et al. | |
| 6,911,039 B2 | 6/2005 | Shiu | |
| 6,974,471 B2 | 12/2005 | Van et al. | |
| 6,997,939 B2 * | 2/2006 | Linder | A61F 2/013 606/200 |
| 7,081,132 B2 | 7/2006 | Cook et al. | |
| 7,147,661 B2 | 12/2006 | Chobotov et al. | |
| 7,655,034 B2 | 2/2010 | Mitchell et al. | |
| 7,682,380 B2 * | 3/2010 | Thornton | A61F 2/07 623/1.13 |
| 7,837,724 B2 | 11/2010 | Keeble et al. | |
| 7,938,851 B2 | 5/2011 | Olson et al. | |
| 7,976,575 B2 | 7/2011 | Hartley | |
| 7,998,186 B2 | 8/2011 | Hartley | |
| 8,012,193 B2 | 9/2011 | Hartley et al. | |
| 8,167,927 B2 | 5/2012 | Chobotov | |
| 8,236,040 B2 * | 8/2012 | Mayberry | A61F 2/97 623/1.11 |
| 8,241,346 B2 | 8/2012 | Chobotov | |
| 8,257,431 B2 | 9/2012 | Henderson et al. | |
| 8,262,671 B2 | 9/2012 | Osypka | |
| 8,328,861 B2 | 12/2012 | Martin et al. | |
| 8,361,135 B2 | 1/2013 | Dittman | |
| 8,475,513 B2 | 7/2013 | Sithian | |
| 8,480,725 B2 | 7/2013 | Rasmussen et al. | |
| 8,641,752 B1 * | 2/2014 | Holm | A61F 2/966 623/1.12 |
| 8,968,384 B2 | 3/2015 | Pearson et al. | |
| 9,060,895 B2 | 6/2015 | Hartley et al. | |
| 9,132,025 B2 | 9/2015 | Aristizabal et al. | |
| 9,254,204 B2 | 2/2016 | Roeder et al. | |
| 9,308,349 B2 | 4/2016 | Rezac et al. | |
| 9,364,359 B2 | 6/2016 | Crawford et al. | |
| 9,375,308 B2 * | 6/2016 | Norris | A61F 2/95 |
| 9,498,361 B2 | 11/2016 | Roeder et al. | |
| 9,585,743 B2 | 3/2017 | Cartledge et al. | |
| 9,585,774 B2 | 3/2017 | Aristizabal et al. | |
| 9,592,143 B2 * | 3/2017 | Shaw | A61F 2/82 |
| 9,681,968 B2 | 6/2017 | Goetz et al. | |
| 9,687,371 B2 | 6/2017 | Buckley et al. | |
| 9,700,701 B2 | 7/2017 | Benjamin et al. | |
| 9,770,322 B2 * | 9/2017 | Burkart | A61F 2/97 |
| 9,782,284 B2 | 10/2017 | Hartley et al. | |
| 9,937,070 B2 | 4/2018 | Skelton et al. | |
| 10,195,063 B2 | 2/2019 | Buckley et al. | |
| 10,610,395 B2 * | 4/2020 | Shaw | A61F 2/82 |
| 10,695,203 B2 * | 6/2020 | Buckley | A61F 2/07 |
| 11,413,177 B2 * | 8/2022 | Lostetter | A61F 2/97 |
| 2001/0020184 A1 | 9/2001 | Dehdashtian et al. | |
| 2002/0029077 A1 | 3/2002 | Leopold et al. | |
| 2003/0120333 A1 | 6/2003 | Ouriel et al. | |
| 2004/0167618 A1 | 8/2004 | Shaolian et al. | |
| 2004/0243221 A1 | 12/2004 | Fawzi et al. | |
| 2005/0149081 A1 | 7/2005 | Ricota et al. | |
| 2006/0002851 A1 | 1/2006 | Langstrom et al. | |
| 2006/0025850 A1 | 2/2006 | Feller et al. | |
| 2006/0025851 A1 | 2/2006 | Khan et al. | |
| 2007/0050015 A1 | 3/2007 | O'Brien et al. | |
| 2009/0099649 A1 | 4/2009 | Chobotov et al. | |
| 2009/0125095 A1 | 5/2009 | Bui et al. | |
| 2009/0299462 A1 | 12/2009 | Fawzi et al. | |
| 2011/0130828 A1 | 6/2011 | Sithian | |
| 2012/0296360 A1 * | 11/2012 | Norris | A61F 2/97 606/191 |
| 2013/0123900 A1 * | 5/2013 | Eblacas | A61F 2/95 623/1.13 |
| 2013/0211501 A1 | 8/2013 | Buckley et al. | |
| 2013/0245742 A1 * | 9/2013 | Norris | A61F 2/07 623/1.11 |
| 2013/0338760 A1 | 12/2013 | Aristizabal et al. | |
| 2016/0100969 A1 * | 4/2016 | Lesmeister | A61F 2/07 623/1.12 |
| 2017/0172724 A1 | 6/2017 | Cartledge et al. | |
| 2017/0281382 A1 | 10/2017 | Lostetter et al. | |
| 2017/0290689 A1 | 10/2017 | Buckley et al. | |
| 2019/0167458 A1 | 6/2019 | Buckley et al. | |
| 2020/0170777 A1 | 6/2020 | Chung et al. | |
| 2020/0306068 A1 * | 10/2020 | Buckley | A61F 2/97 |

FOREIGN PATENT DOCUMENTS

| | | |
|---|---|---|
| EP | 1441668 B1 | 1/2008 |
| EP | 2111828 A2 | 10/2009 |
| EP | 1915113 B1 | 3/2010 |
| EP | 1358903 B1 | 11/2011 |
| EP | 1474074 B1 | 4/2014 |
| EP | 2749251 B1 | 7/2016 |
| EP | 2956198 B1 | 11/2017 |
| JP | 2006-034970 A | 2/2006 |
| JP | 2009-505747 A | 2/2009 |
| JP | 2010-540190 A | 12/2010 |
| JP | 2015-506805 A | 3/2015 |
| WO | 03/45284 A2 | 6/2003 |
| WO | 2004/047885 A2 | 6/2004 |
| WO | 2007/025101 A2 | 3/2007 |
| WO | 2009/046372 A2 | 4/2009 |
| WO | 2009/058369 A1 | 5/2009 |
| WO | 2013/122707 A1 | 8/2013 |
| WO | 2014/096811 A2 | 6/2014 |
| WO | 2018/222494 A1 | 12/2018 |

OTHER PUBLICATIONS

International Preliminary Report on Patentability received for PCT Patent Application No. PCT/US2013/021528, dated Aug. 28, 2014, 8 pages.

(56) References Cited

OTHER PUBLICATIONS

International Preliminary Reporton Patentability received for PCT Patent Application No. PCT/US2018/034399, dated Dec. 12, 2019, 9 pages.
International Search Report & Written Opinion from PCT/US2018/034399, dated Nov. 9, 2018, 13 pages.
International Search Report and Written Opinion received for PCT Patent Application No. PCT/US2013/021528, dated Jun. 19, 2013, 11 pages.

* cited by examiner

ENDOPROSTHESIS HAVING ALIGNED LEGS FOR EASE OF CANNULATION

CROSS-REFERENCE TO RELATED APPLICATION

This application is a continuation of U.S. patent application Ser. No. 16/266,308, filed Feb. 4, 2019, now U.S. Pat. No. 10,695,203, issued Jun. 30, 2020, which is a continuation of U.S. patent application Ser. No. 15/632,741, filed Jun. 26, 2017, now U.S. Pat. No. 10,195,063, issued Feb. 5, 2019, which is a divisional of U.S. patent application Ser. No. 13/740,457, filed Jan. 14, 2013, now U.S. Pat. No. 9,687,371, granted Jun. 27, 2017, which claims priority to and the benefit of U.S. Provisional Patent Application Ser. No. 61/598,773, filed Feb. 14, 2012, all of which are incorporated by reference herein in their entireties.

FIELD

The present disclosure relates to improved branched endoprostheses for treating disease of the vasculature.

DISCUSSION OF THE RELATED ART

Branched endoprostheses are commonly used for treating disease of the vasculature. By way of example, bifurcated stent grafts may be used in the treatment of abdominal aortic aneurisms, which generally affect the abdominal aorta and may extend down into the iliac arteries.

A bifurcated stent graft used in the treatment of abdominal aortic aneurisms is generally inserted through an iliac artery up into the abdominal aorta, where it is deployed and anchored. The graft's ipsilateral leg extends down into the iliac artery through which the graft was inserted. On the other hand, the graft's contralateral leg does not extend below the abdominal aorta.

To extend the graft's contralateral leg down into the other iliac artery, a second stent graft is inserted through that other iliac artery over a guidewire and attached to the original graft's contralateral leg. Although endoscopic imaging, radiopaque markers, etc. may be employed, this cannulation process is often difficult given not only the tortuous vasculature, but also structural biases within the original stent graft angling the legs apart in a Y configuration so as to face them toward their respective iliac arteries.

Generally speaking, cannulation of contralateral legs of branched endoprostheses presents difficulties for medical practitioners who heretofore have had to rely heavily on trial and error. There is thus a need in the art for bifurcated endoprostheses that are better adapted for ease of cannulation.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Figure 1A:
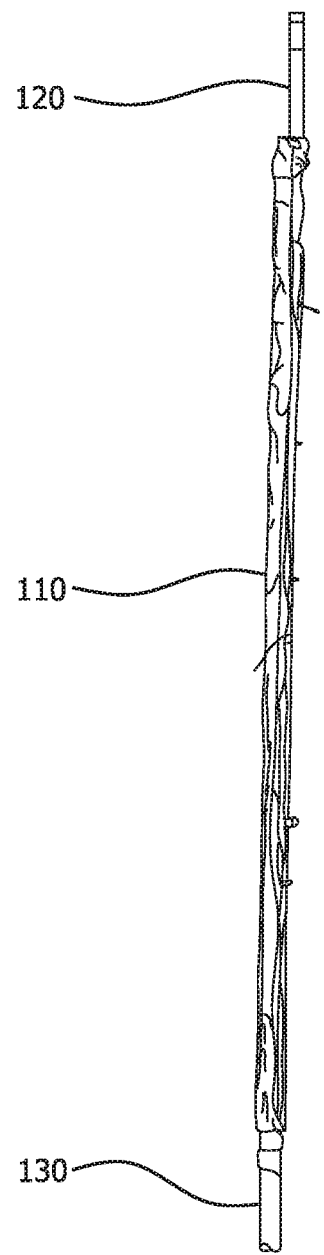
FIGS. 1A-1E illustrate the progressive deployment of a branched endoprosthesis having two legs in an aligned configuration in accordance with one embodiment of the present disclosure.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

In addition, the present disclosure will be described primarily with reference to treating disease of the abdominal aorta, however, the disclosure and principles may be applied to other disease of the vasculature, including, for example, any disease where a larger vessel and one or more branch vessels are to be treated. Likewise, although the disclosure will be described primarily with reference to bifurcated endoprostheses, it should be understood that the disclosure and principles may be applied to endoprostheses having any number of branches, for example, 2, 3, 4 or more.

The present disclosure is directed toward a branched endoprosthesis. An endoprosthesis may comprise a graft component and at least one support component, such as in a stent graft.

A graft component is generally any abluminal (i.e., outer, vessel surface) or luminal (i.e., inner, blood flow surface) covering configured to partially or substantially cover one or more support components.

In various embodiments, a graft component comprises ePTFE. However, other useful materials for the graft component may comprise one or more of nylons, polycarbonates, polyethylenes, polypropylenes, polytetrafluoroethylenes, polyvinyl chlorides, polyurethanes, polysiloxanes, and other biocompatible materials.

A graft component is fixedly secured or otherwise coupled at a single or a plurality of locations to the abluminal or luminal surface of the support component, for example, using one or more of taping, heat shrinking, adhesion and other processes known in the art. In some embodiments, a plurality of graft components are used and may be coupled to both the abluminal and luminal surfaces of the support component(s). In other embodiments, a plurality of graft components "sandwich" the support component(s), the graft components being attached to each other.

In various embodiments, a support component has dimensions appropriate for the given treatment and may provide structural support for the graft component of the endoluminal device and/or the vasculature to be treated. A support component may be a stent comprised either of a wire having a helical configuration or be comprised of one or a plurality of rings. Among other configurations, the wire or a ring itself may be linear or have a sinusoidal or zig-zag pattern. Still another support component may be cut from a tube and have any pattern suitable for the treatment.

The support component can be comprised of a shape-memory material, such as nitinol. In other embodiments, however, the support component may be comprised of other materials, self-expandable or otherwise expandable (e.g., with a conventional balloon catheter or spring mechanism), such as various metals (e.g., stainless steel), alloys and polymers.

In various embodiments, the branched endoprosthesis comprises a body portion and at least two leg portions, which may be defined by the graft and/or support components. The cross-section of the body portion may be circular, ovoidal, or have polygonal features with or without curved features. The cross-sectional shape of the body portion may be either substantially constant or variable along its axial length. In like manner, the cross-sectional surface area of the body portion may be either substantially constant or variable along its axial length. In an embodiment of a bifurcated endoprosthesis, the body portion's cross-section is substantially circular at its distal end but tapers to have an ovoidal rectangular cross-section with a smaller cross-sectional surface area in its bifurcation region.

As noted previously, a branched endoprosthesis comprises two or more leg portions branched off of and in luminal communication with the body portion.

In various embodiments, the axial length(s) of the contralateral leg(s) (i.e., the leg(s) for cannulation) is/are substantially shorter that the axial length of the ipsilateral leg.

In various embodiments, a branched endoprosthesis possesses one or more structural biases angling the leg portions apart, for instance in a Y configuration, so as to face or direct them toward their respective vessels to be treated. The structural bias may arise from either or both of a graft component and a support component.

In various embodiments, at least two leg portions are in an aligned configuration for ease of cannulation. The alignment may be permanent or in some embodiments, temporary until after guidewire insertion or cannulation. In various embodiments, aligning a plurality of leg portions requires overcoming the aforementioned structural bias. As used herein, "align" or "aligned" means aligned axially, drawn together, parallel, and/or the state of the plane of the contralateral leg's opening being perpendicular to the axis of the ipsilateral leg. For the avoidance of doubt, "align" may, but does not necessarily implicate alignment along or with respect to any anatomical or endoprosthesis axis.

In an embodiment, alignment is accomplished by commonly sheathing the legs and only removing the sheath after guidewire insertion or cannulation. For example, and with reference to the accompanying drawings, FIG. 1A illustrates an outer sheath 110 enclosing a bifurcated stent graft (not shown) to be delivered via a guidewire 120 and a tubular element 130.

A "sheath" may be comprised of one or more of nylons, polycarbonates, polyethylenes, polypropylenes, polytetrafluoroethylenes, polyvinyl chlorides, polyurethanes, polysiloxanes, stainless steels, or other biocompatible materials. A sheath can be a sleeve or an introducer sheath. In yet other embodiments, a sheath is a tubular element, as that term has been defined herein.

The term "tubular element" includes any longitudinally extending structure with or without a lumen therethrough, for example a catheter. Thus, tubular elements include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Tubular elements can be of any material and can have any cross-sectional shape including but not limited to profiles that are circular, oval, triangular, square, polygon shaped or randomly shaped.

Figure 1B:
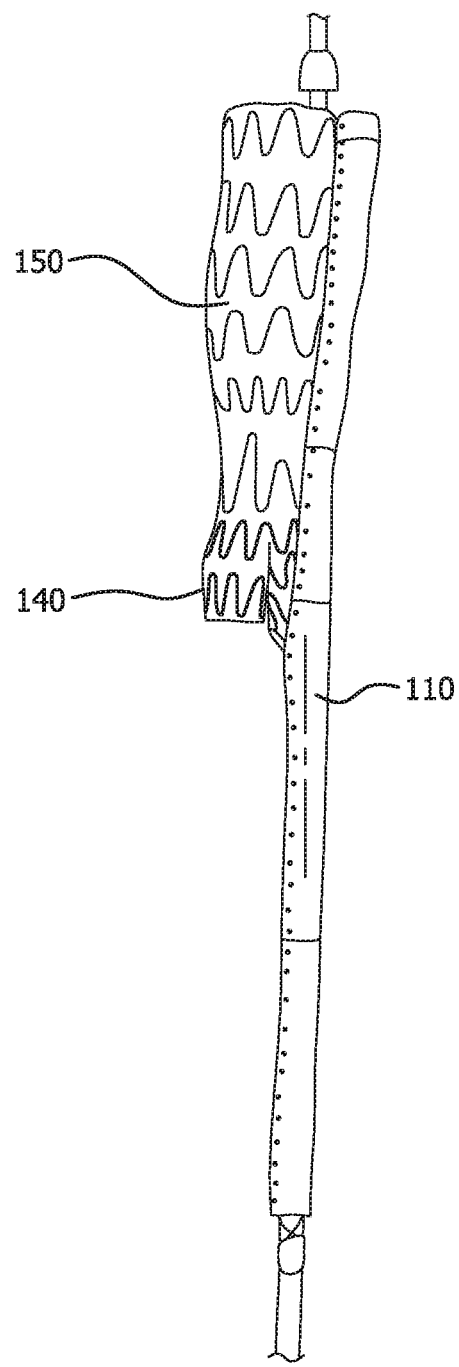

Turning now to FIG. 1B, outer sheath 110 may be partially removed from the distal half of bifurcated stent graft 140, revealing a closed inner sheath 150 which aligns the contralateral and ipsilateral legs of bifurcated stent graft 140.

Figure 1C:
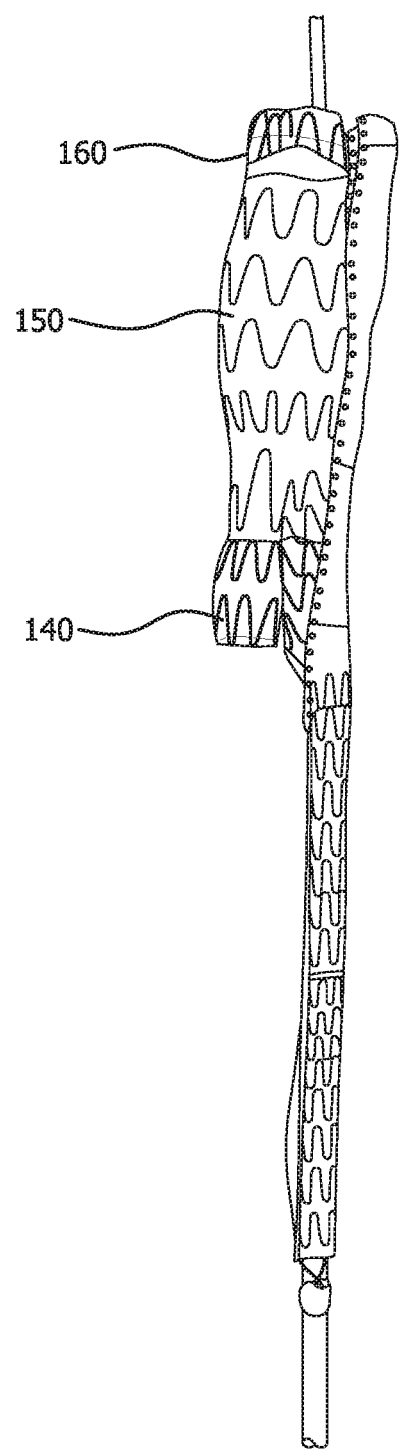

With reference to FIG. 1C, anchors 160 at the distal end of bifurcated stent graft 140 may be retracted for adjusting placement of bifurcated stent graft 140. Note that in this embodiment, inner sheath 150 still maintains the contralateral and ipsilateral legs of bifurcated stent graft 140 in an aligned configuration.

Figure 1D:
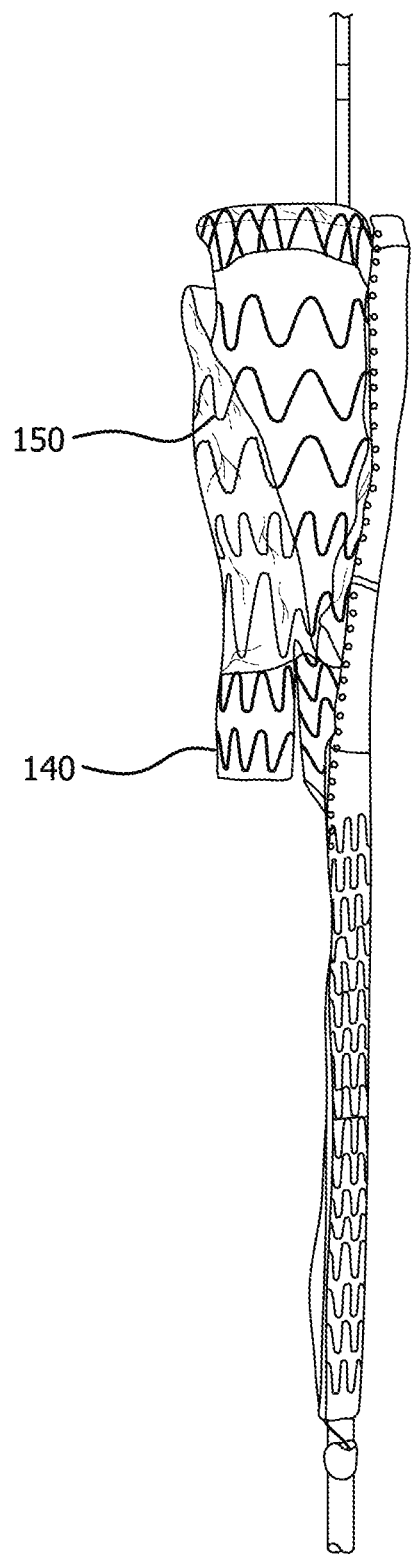
Figure 1E:
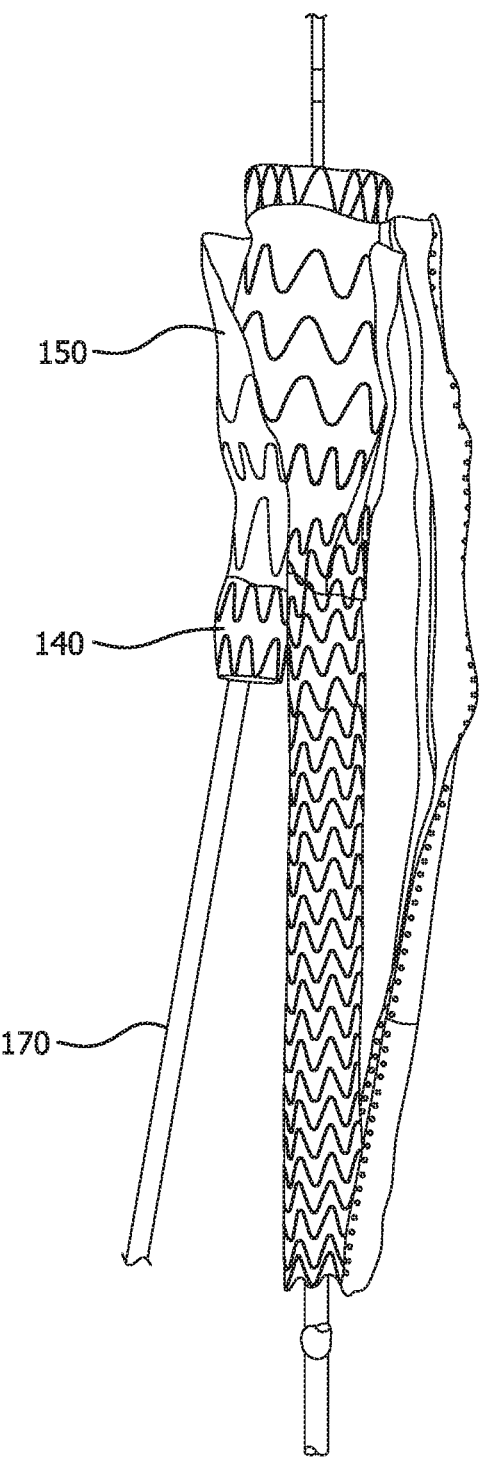

As shown in FIG. 1D, inner sheath 150 may be partially removed from the distal portion of bifurcated stent graft 140, but not removed at its proximal end, thus maintaining the contralateral and ipsilateral legs of bifurcated stent graft 140 in an aligned configuration until, as shown in FIG. 1E, a guidewire 170 has been inserted into the contralateral leg of bifurcated stent graft 140 or cannulation of the contralateral leg has occurred.

Notwithstanding the foregoing non-limiting example, various physical and chemical coupling methods and apparatuses may be used in the alignment, including but not limited to various removable tethers, restraints, adhesives, hooks, magnets, nanostructure binding agents, etc.

Figure 2B:
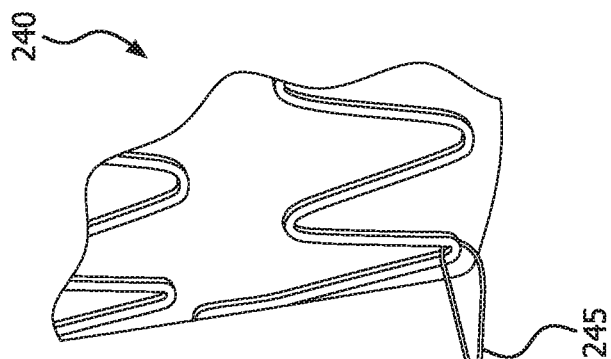
FIGS. 2A and 2B illustrate a tether configured to maintain contralateral and ipsilateral legs of a bifurcated stent graft in an aligned configuration in accordance with one embodiment of the present disclosure.
Figure 2B:
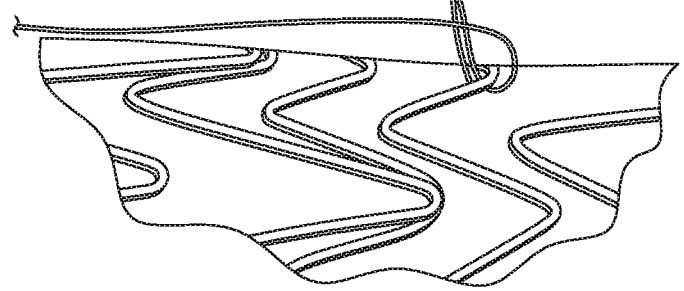
Figure 2A:
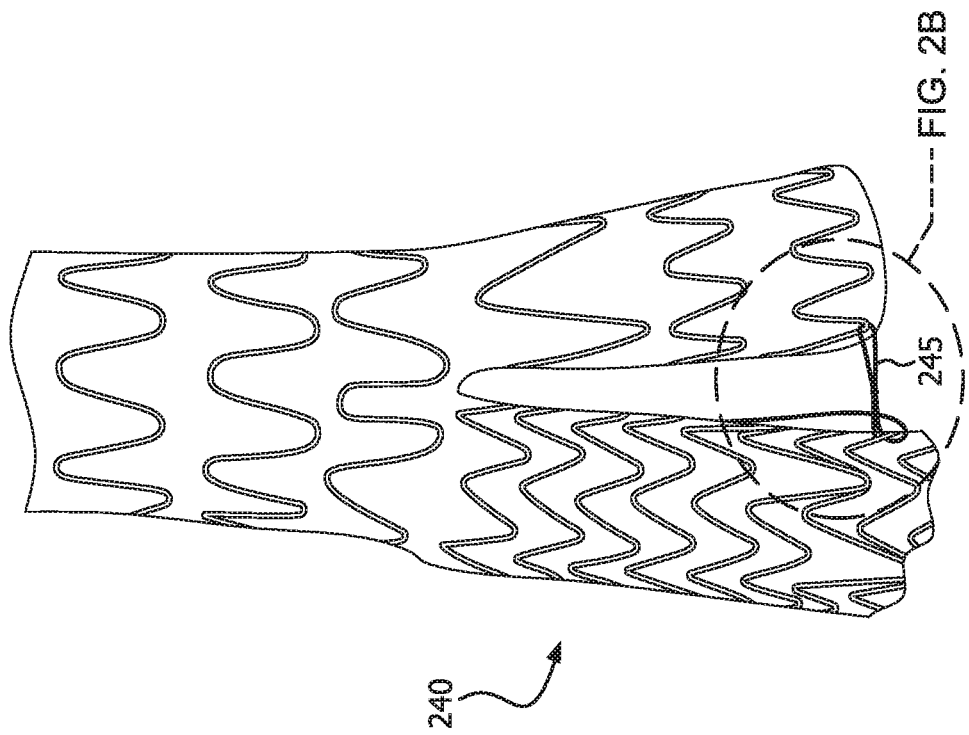

FIGS. 2A and 2B illustrate a tether 245 configured to maintain contralateral and ipsilateral legs of a bifurcated stent graft 240 in an aligned configuration in accordance with one embodiment of the present disclosure. In various embodiments, tether 245 releasably couples and retains contralateral and ipsilateral legs of bifurcated stent graft 240 including, in various embodiments, during movement of bifurcated stent graft 240 between delivery and deployed configurations.

In various embodiments, an outer sheath extends around and maintains bifurcated stent graft 240 in a delivery configuration. In such embodiments, the outer sheath can have opposite sides releasably held together to maintain bifurcated stent graft 240 in the delivery configuration. In such embodiments, the outer sheath can have a plurality of holes through which an elongated member extends to releasably hold the opposite sides of the outer sheath together. In such embodiments, tether 245 can be an extension of the elongated member.

An end tail of tether 245 can be tucked under undeployed portions of a surrounding sleeve and/or routed under, or otherwise secured to, one or more apices of a support component. Tether 245 can be routed in various configurations, for example between an apice of a support component and the wall of a graft component. In general, an end tail of tether 245 is routed so as to be retained, while not presenting high pullout forces.

Tether 245 can comprise a thread, fiber, or filament, for example one that is polymeric in nature. In other embodiments, tether 245 comprises a wire, having a high columnar strength. In yet other embodiments, tether 245 is a tubular element, as that term has been defined herein.

In various embodiments, tether 245 is adjustable separate from being pulled out. In various embodiments, tether 245 is pulled out separate from deployment of bifurcated stent graft 240.

In various embodiments, tethering eliminates the need for an inner sheath, thus reducing the crossing profile, for example to less than 18 Fr, less than 16 Fr, or less than 14 Fr.

Adhesives may comprise those that are soluble for releasing the legs from their aligned configuration after guidewire insertion or cannulation. A single hook or a plurality of hooks or hook and loop fasteners (e.g., a Velcro® type configuration) may be used. A magnet may be inserted via catheter into the one leg to draw another leg into alignment with it. Nanostructure binding agents useful in the alignment may comprise DNA, RNA, etc.

Additional features and elements may be used in connection with the present disclosure. In one embodiment for example, at least one leg is maintained in an open configuration for ease of cannulation. This may be accomplished, for example, by incorporating an independent wire or ring, such as a support component as described herein, at the distal end of the leg. In an embodiment, a plurality of serially aligned support components are adapted to hold the contralateral leg open for cannulation. In yet another embodiment, one or more radiopaque and/or echogenic markers are incorporated into the branched endoprosthesis, for example, along, or at the distal end of, the contralateral leg.

A cannulation method comprises delivering a branched stent graft enclosed by an outer sheath into a branch artery and to the lumen of a trunk artery via a guidewire and a tubular element, for example at a distal end of a catheter.

In various embodiments, the outer sheath is partially removed from the body portion of the branched stent graft extending into the trunk artery, thus partially deploying the graft and exposing an inner sheath which aligns one or more contralateral legs with the ipsilateral leg of the branched stent graft.

Next, placement of the branched stent graft may be adjusted, for example, by retracting anchors at the distal end of the body portion of the branched stent graft, rotating and/or advancing or reversing the guidewire and/or the tubular element, and thereafter fully deploying the anchors into the sides of the trunk artery.

Once the branched stent graft is determined to be properly positioned, a second guidewire may be inserted into a contralateral leg of the branched stent graft via a second branch artery in communication with the trunk artery. Cannulation of the contralateral leg may thereafter occur.

Once the second guidewire has been inserted into the contralateral leg, the inner sheath may be fully removed, thus no longer necessarily maintaining the contralateral and ipsilateral legs of the branched stent graft in an aligned configuration.

Yet another method comprises providing a branched stent graft comprising a body portion, an ipsilateral leg portion, and a contralateral leg portion. In this particular embodiment, the leg portions may be biased to be angled apart in a Y configuration. Next, the bias is temporarily overcome by aligning the leg portions using one or more of the mechanisms described herein.

In accordance with this method, the branched stent graft is delivered to a trunk vessel via an ipsilateral branch vessel. The body portion and the ipsilateral leg portion of the branched stent graft are deployed in the trunk vessel and the ipsilateral branch vessel respectively. Using the alignment of the leg portions, a distal opening of the contralateral leg portion is located to facilitate its cannulation. Finally, the leg portions are allowed to return to the initial Y configuration.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device comprising:
   an endoprosthesis including a first portion and a second portion; and
   an outer sheath extending around and maintaining the endoprosthesis in a delivery configuration;
   an elongated member releasably holding the outer sheath around the endoprosthesis and further comprising an extension of the elongated member which releasably couples the first portion with the second portion to assist in maintaining a parallel alignment of the first portion with the second portion during deployment of the endoprosthesis,
   wherein the elongated member is adjustable to release the outer sheath separate from adjustment of the extension to permit the deployment of the endoprosthesis without decoupling the first portion from the second portion.

2. The medical device of claim 1, wherein the outer sheath has opposite sides releasably held together by the elongated member to maintain the endoprosthesis in the delivery configuration.

3. The medical device of claim 2, wherein the outer sheath has a plurality of holes through which the elongated member extends to releasably hold the opposite sides of the outer sheath together.

4. The medical device of claim 1, wherein the elongated member is adapted to be releasable after the endoprosthesis is deployed via releasing the outer sheath.

5. The medical device of claim 1, wherein the first portion and the second portion are structurally biased to angle apart from one another, and wherein the elongated member is adapted to temporarily overcome the bias to assist in maintaining alignment of the first and second portions during deployment of the endoprosthesis.

6. The medical device of claim 1, further comprising a sleeve surrounding the endoprosthesis, wherein the elongated member has an end tail tucked under undeployed portions of the sleeve.

7. The medical device of claim 1, wherein the endoprosthesis includes a graft component and at least one support component coupled with the graft component.

8. The medical device of claim 7, wherein the elongated member has an end tail routed under one or more apices of the at least one support component.

9. The medical device of claim 1, wherein the elongated member comprises a thread, fiber, or filament.

10. The medical device of claim 1, wherein the elongated member is polymeric.

11. The medical device of claim 1, wherein the elongated member comprises a wire having a high columnar strength.

12. The medical device of claim 1, wherein the elongated member is adapted to be adjustable separate from being removed from the endoprosthesis.

13. The medical device of claim 12, wherein the elongated member is adapted to be adjustable to adjust the alignment of the first and second portions of the endoprosthesis.

14. The medical device of claim 1, wherein the first portion is a first leg of the endoprosthesis and wherein the second portion is a second leg of the endoprosthesis.

\* \* \* \* \*